United States Patent
Powell et al.

(10) Patent No.: US 10,595,885 B2
(45) Date of Patent: Mar. 24, 2020

(54) SURGICAL DRILL GUIDE

(71) Applicant: Arthrex, Inc., Naples, FL (US)

(72) Inventors: Chris M. Powell, Naples, FL (US); Matthew Palmer, Medford, MA (US)

(73) Assignee: Arthrex, Inc., Naples, FL (US)

( * ) Notice: Subject to any disclaimer, the term of this patent is extended or adjusted under 35 U.S.C. 154(b) by 140 days.

(21) Appl. No.: 15/693,516

(22) Filed: Sep. 1, 2017

(65) Prior Publication Data

US 2019/0069910 A1    Mar. 7, 2019

(51) Int. Cl.
| | |
|---|---|
| A61B 17/17 | (2006.01) |
| A61B 17/064 | (2006.01) |
| A61B 17/068 | (2006.01) |
| A61B 17/84 | (2006.01) |
| A61B 17/68 | (2006.01) |
| A61B 17/10 | (2006.01) |
| A61B 17/00 | (2006.01) |
| A61B 17/072 | (2006.01) |

(52) U.S. Cl.
CPC .......... *A61B 17/17* (2013.01); *A61B 17/0642* (2013.01); *A61B 17/0682* (2013.01); *A61B 17/10* (2013.01); *A61B 17/84* (2013.01); *A61B 2017/00668* (2013.01); *A61B 2017/0645* (2013.01); *A61B 2017/07264* (2013.01); *A61B 2017/681* (2013.01)

(58) Field of Classification Search
CPC .......... A61B 2017/00668; A61B 2017/07264; A61B 2017/07285; A61B 17/064; A61B 17/0642; A61B 17/068; A61B 17/0682; A61B 17/115; A61B 17/1152
USPC .......................................................... 606/96
See application file for complete search history.

(56) References Cited

U.S. PATENT DOCUMENTS

| | | | |
|---|---|---|---|
| 5,769,856 | A | 6/1998 | Dong et al. |
| 6,083,225 | A * | 7/2000 | Winslow .............. A61B 17/025 606/279 |
| 6,960,216 | B2 | 11/2005 | Kolb et al. |
| 7,094,242 | B2 | 8/2006 | Ralph et al. |
| 7,416,553 | B2 | 8/2008 | Patel et al. |
| 7,909,829 | B2 | 3/2011 | Patel et al. |
| 7,935,123 | B2 | 5/2011 | Fanger et al. |
| 2013/0213843 | A1 | 8/2013 | Knight et al. |
| 2015/0282819 | A1 * | 10/2015 | Austin .................. A61B 17/17 606/96 |
| 2016/0310125 | A1 | 10/2016 | Spivey et al. |

OTHER PUBLICATIONS

International Search Report and Written Opinion for PCT Application No. PCT/US2018/048764 dated Nov. 27, 2018.

* cited by examiner

*Primary Examiner* — David W Bates
*Assistant Examiner* — Marcela I Shirsat
(74) *Attorney, Agent, or Firm* — Carlson, Gaskey & Olds, P.C.

(57) ABSTRACT

Drill guides are disclosed herein that allow an implant to be partially inserted after the holes are drilled and before the drill guide has been removed from the surgical location.

15 Claims, 1 Drawing Sheet

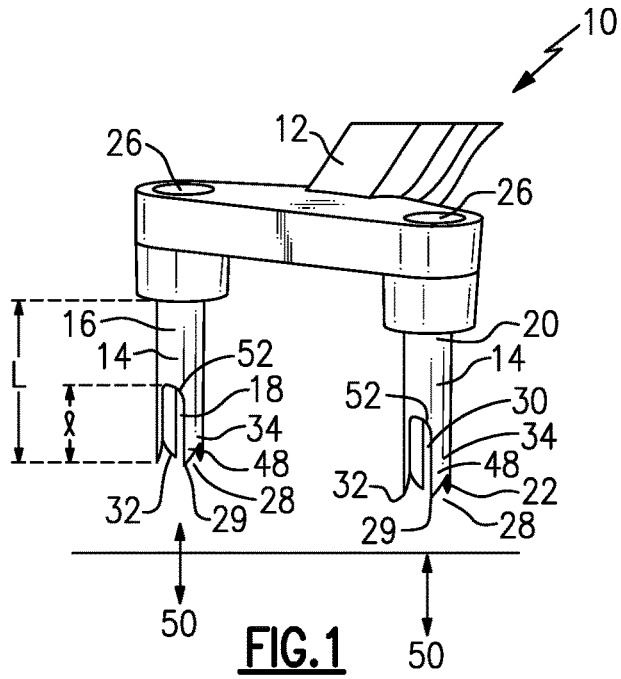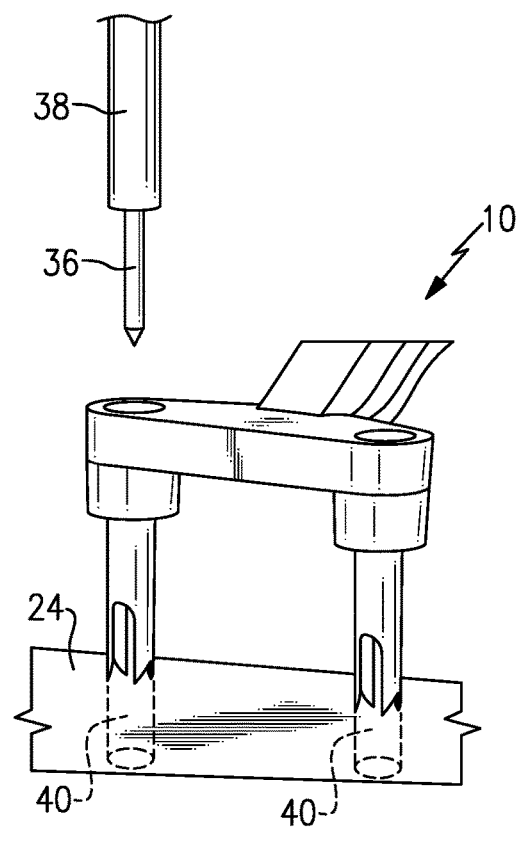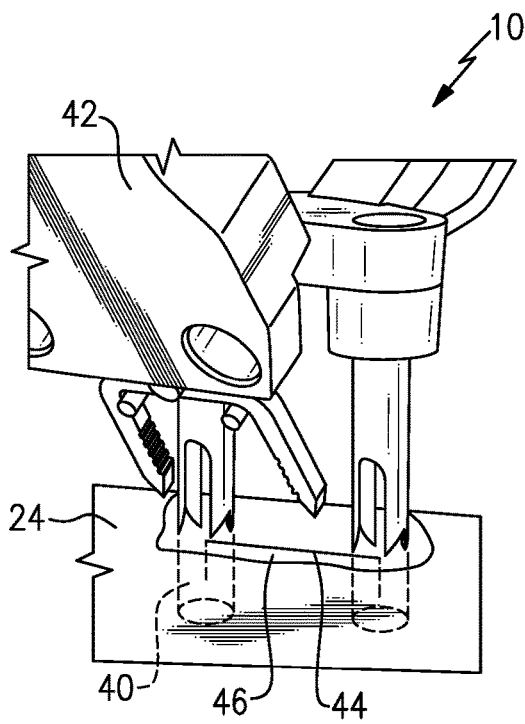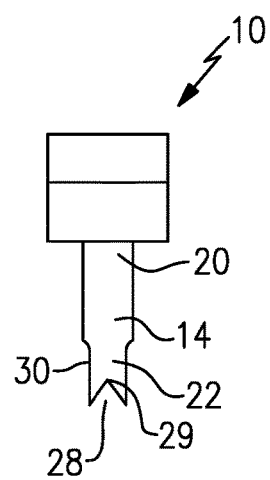

SURGICAL DRILL GUIDE

BACKGROUND

This disclosure relates to surgical drill guides.

SUMMARY

Surgical drill guides are disclosed that allow holes to be drilled into bone at a desired location. Holes are drilled in the bone through referencing holes of the drill guide. A drill guide can be used for guiding a drilling tool (e.g., a drill bit) during formation of one or more holes in bone. A drill guide can be made out of metal (e.g., stainless steel), hard polymeric material, ceramic material, composite material, or any other material. Furthermore, a drill guide can be formed in any suitable fashion (e.g., casting, milling, etc.). Additionally, a drill guide can have various sizes and shapes, depending on the size and shape of a patient's anatomy, etc.

Drill guides as disclosed herein allow an implant to be partially inserted after the holes are drilled and before the drill guide has been removed from the surgical location. With the disclosed drill guides, alignment pins are not required. Since a drill guide is not removed until the implant is partially inserted, the location of the drilled hole(s) is not lost. Thereby, embodiments of methods disclosed herein include the specific exclusion of alignment pins. Various implants can be utilized with the disclosed drill guides.

In an embodiment, a drill guide includes a handle including one or more openings. In an embodiment, the drill guide includes an alignment tube defines a drill passage, and the drill passage aligns with the opening of the handle. The alignment tube can have a substantially cylindrical shape. The alignment tube can have different shapes. In an embodiment, the shape of the alignment tube can be based on the shape of a desired implant. An alignment tube can include a window to allow access to a drill passage. An alignment tube can include a first end region attached to the handle and a second end region having a bottom surface that can contact bone. A window can extend from a bottom surface of the second end region of the alignment tube.

Methods of performing surgery utilizing drill guides are also disclosed herein. In particular, the methods disclosed herein utilize the disclosed drill guides without the need for alignment pins. For example, a method includes inserting a securing member of an implant through a window of a drill guide's alignment tube. Thereby, the securing member is received in a bone hole to attach the implant to the bone while the drill guide is still positioned relative to the bone.

BRIEF DESCRIPTION OF THE DRAWINGS

FIG. 1 illustrates a schematic perspective view of an embodiment of a drill guide;

FIG. 2 illustrates a schematic perspective view of an embodiment of the drill guide positioned on bone;

FIG. 3 illustrates a schematic perspective view of an embodiment of a drill guide and grasper; and FIG. 4 illustrates a side view of an embodiment of a drill guide.

DETAILED DESCRIPTION

Surgical drill guides allow surgeons to accurately drill holes in a bone at a desired location. After drilling a hole, an alignment pin can be placed into the drilled hole to allow the surgeon to find the location of the hole during surgery. When an implant is to be inserted into the hole, the alignment pin is removed to allow the implant to be attached to the bone with a securing member received in the hole in the bone. However, once the alignment pin is removed, it may be difficult for the surgeon to again find the location of the drilled hole.

Disclosed herein are drill guides that allow an implant to be partially inserted after the holes are drilled and before the drill guide has been removed from the surgical location. Thereby, alignment pins are not required. Since a drill guide is not removed until the implant is partially inserted, the location of the drilled hole(s) is not lost. Various implants can be utilized with the disclosed drill guides. In an embodiment, an implant can be a compression staple. In an embodiment, a compression staple comprises a shape memory material (e.g., nitinol).

A drill guide includes a handle including one or more openings. In an embodiment, an opening can be substantially v-shaped, with or without defined teeth. In an embodiment, a handle includes at least one opening that aligns with a drill passage of at least one alignment tube.

In an embodiment, at least one alignment tube extends from an opening in the handle. An alignment tube can include a first end region attached to the handle and a second end region having a bottom surface that can contact bone. In an embodiment, a drill guide includes a handle including two openings and two alignment tubes.

Alignment tubes can have different shapes, including substantially cylindrical. In embodiments with two or more alignment tubes, the tubes can be the same or different shapes. In an embodiment, the shape of the alignment tube can be based on the shape of a desired implant or based on the anatomy of the bone to be drilled.

An alignment tube can also include a window to allow access to a drill passage. At least one window can extend from a bottom surface of a second end region of an alignment tube. In an embodiment, an alignment tube includes two windows aligned with each other. A bottom surface of a second end region can be roughened and/or include teeth to engage bone. In an embodiment, a bottom surface of the second end region includes openings. In an embodiment, an alignment tube has a first length and a window has a second length, whereby the second length is less than half the first length.

In another embodiment, the alignment tube includes a body that defines a drill passage, and a portion of the body is located between two windows. A bottom surface of the portion of the body includes teeth.

Methods include performing surgery utilizing the drill guides disclosed herein. In particular, the methods disclosed herein utilize the disclosed drill guides without the need for alignment pins. For example, a method includes inserting a securing member of an implant through a window of a drill guide's alignment tube. Thereby, the securing member is received in a bone hole to attach the implant to the bone while the drill guide is still positioned relative to the bone. In an embodiment, a method includes drilling a hole into at least one bone after a drill guide is positioned relative to the bone(s). For example, a drill guide can be positioned relative to a bone, and a drill bit of a drilling instrument can be introduced into an alignment tube. The drill bit can proceed through the alignment tube until the drill bit contacts bone. The drill bit can then be used to create a hole in the bone having a desired shape and size. An alignment tube can be of a size and/or shape to match a desired size and/or shape of a desired hole in the bone. Methods as disclosed herein can be performed in bones of the foot, ankle, wrist, hand, legs, arms, etc. Additionally, methods as disclosed herein can be performed during surgery of humans, dogs, cats, horses, etc.

After the securing member of the implant is inserted into the bone and secures the implant to the bone, the drill guide can be removed from its position relative to the bone. In one example, no alignment pins are utilized. In one example, a bottom surface of the alignment tube includes teeth or a roughened surface to engage the bone. In one example, the alignment tube has a substantially cylindrical shape. In one example, the window extends from a bottom surface of the alignment tube. In one example, each opening is substantially v-shaped.

FIG. 1 illustrates a perspective view of a drill guide 10. The drill guide 10 includes a handle 12 that can be grasped and two alignment tubes 14. Each alignment tube 14 includes a body 16 that defines a drill passage 18, a first end region 20 attached to the handle 12, and a second end region 22 that can contact bone 24. The handle 12 includes two openings 26, and the drill passage 18 of one alignment tube 14 is aligned with one of the openings 26 of the handle 12. The drill guide 10 can be made out of metal (e.g., stainless steel), hard polymeric material, ceramic material, composite material, or any other material. Furthermore, the drill guide 10 can be formed in any suitable fashion (e.g., casting, milling, etc.). Additionally, the drill guide 100 can have various sizes and shapes, depending on the size and shape of a patient's anatomy, etc.

The alignment tubes 14 have a substantially cylindrical shape. The second end region 22 includes a bottom surface 32 having a feature that increases traction with the bone 24 to prevent the handle 12 from sliding or moving relative to the bone 24. In one example, the bottom surface 32 is roughened or non-smooth. In one example, the bottom surface 28 of the second end region 22 includes teeth 29 that are defined by openings 28. In another example, the openings 28 are substantially v-shaped.

Each alignment tube 14 includes a window 30 that allows access to the drill passage 18 of the alignment tube 14 from outside the alignment tube 14. The window 30 is elongated and extends from the bottom surface 32 of the second end region 22 of the alignment tube 14. In one example, the window 30 is defined by two side surfaces 48 substantially parallel to a longitudinal axis 50 of the alignment tube 14 and an end surface 52 connecting the two side surfaces 48. In one example, the end surface 52 is curved. In one example, the window 30 has a length l that is less than one half a length of the alignment tube 14. In one example, each alignment tube 14 includes two windows 30 that are aligned with each other such that the drill passage 18 is accessible from both sides of the alignment tube 14. The windows 30 are spaced approximately 180 degrees apart. In this example, a portion 34 of the body 16 is located between the two windows 30, and each portion 34 defines two teeth 29 and the opening 28 located between the two teeth 29.

As shown in FIG. 2, the drill guide 10 is positioned on the bone 24 at a desired location. The teeth 29 grasp the surface of the bone 24. A drill bit 36 of a drill 38 is positioned in the aligned opening 26 and drill passage 18, and the drill bit 36 forms a first hole 40 in the bone 24. After the first hole 40 is drilled, the drill bit 36 is positioned in the other aligned opening 26 and the drill passage 18, and the drill bit 36 forms a second hole 40 in the bone 24. The drill 38 is then removed from the drill guide 10, and the drill guide 10 remains on the bone 24 so that each opening 26 and drill passage 18 are aligned with one of the drilled holes 40.

As shown in FIG. 3, a surgical instrument 42, such as a grasper, is employed to position an implant 46 for attachment to the bone 24. The implant 46 can then be partially attached to the bone 24 by a securing member 44 before the drill guide 10 is removed from the bone 24. The securing member 44 is inserted through the windows 30 of the alignment tubes 14 and into the drilled holes 40 to secure the implant 46 to the bone 24. After the implant 46 is attached to the bone 24, the drill guide 10 can be removed from the bone 24. As the securing member 44 is located in the windows 30, the drill guide 10 can be lifted from the bone 24 without any interaction with the implant 46 or the securing member 44. In one example, the securing member 44 is a compression staple. In an embodiment, the compression staple comprises a shape memory material (e.g., nitinol).

As the drill guide 10 remains on the bone 24 during attachment of the implant 46 to the bone 24, alignment pins are not needed to mark the location of the drilled holes 40 because the drill guide 10 is not removed until the implant 46 is partially attached. The alignment tubes 14 of the drill guide 10 are used to mark the location of the drilled holes 40.

Although a drill guide 10 with two openings 26 and two drill passages 18 that are aligned has been illustrated and described, the drill guide 10 can include any number of opening/drill passages. For example, the drill guide 10 can include a single opening 26 and drill passage 18 that can receive a different type of securing member 44, such as a screw.

In one illustrative embodiment, a drill guide includes a handle including two openings and two alignment tubes each having a substantially cylindrical shape. Each of the two alignment tubes includes a drill passage that aligns with one of the two openings of the handle. The two alignment tubes each include a window to allow access to the drill passage. The two alignment tubes each include a first end region attached to the handle and a second end region having a bottom surface that can contact bone. The windows extend from a bottom surface of the second end region. In one embodiment, the openings are substantially v-shaped.

In another illustrative embodiment, a drill guide can also comprise a handle and at least one alignment tube including a drill passage. The at least one alignment tube includes a window that allows access to the drill passage.

In one embodiment, the handle includes at least one opening that aligns with the drill passage of the at least one alignment tube. In one embodiment, the at least one opening of the handle comprises two openings and the at least one alignment tube comprises two alignment tubes. In one embodiment, the at least one alignment tube is substantially cylindrical. In one embodiment, the at least one alignment tube includes a first end region attached to the handle and a second end region having a bottom surface that can contact bone. In one embodiment, the bottom surface is roughened. In one embodiment, the bottom surface of the second end surface includes openings. In one embodiment, as shown in FIG. 4, the openings are substantially v-shaped and define teeth. In one embodiment, the window extends from the bottom surface of the at least one alignment tube. In one embodiment, the at least one alignment tube has a first length L and the window has a second length l, and the second length l is less than half the first length L. In one embodiment, the at least one alignment tube includes two windows aligned with each other. In one embodiment, a portion of the body is located between the two windows, and a bottom surface of the portion of the body includes teeth.

In another illustrative embodiment, a method of attaching an implant to bone comprising inserting a securing member of an implant through a window of an alignment tube of a drill guide and into a bone while the drill guide is positioned relative to the bone.

In one embodiment, the method includes removing the drill guide from its position relative to the bone after the securing member of the implant is inserted into the bone. In one embodiment, no alignment pins are utilized. In one embodiment, a bottom surface the alignment tube includes teeth to engage the bone. In one embodiment, the alignment tube has a substantially cylindrical shape. In one embodiment, the window extends from a bottom surface of the alignment tube.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason, the following claims should be studied to determine the true scope and content of this invention.

What is claimed is:

1. A drill guide comprising:
    a handle including two openings; and
    two alignment tubes each having a body having a substantially cylindrical shape, a longitudinal axis, a bottom surface, a drill passage that aligns with one of the two openings of the handle, two windows to allow access to the drill passage, two adjacent teeth on the bottom surface, a first end region attached to the handle, and a second end region including the bottom surface and the two adjacent teeth that can contact bone, wherein the two windows extend from the bottom surface of the second end region and each have a length that extends substantially parallel to the longitudinal axis of the respective one of the two alignment tubes, a portion of the body and the two adjacent teeth are located between the two windows, a recess is defined between the two adjacent teeth, and each of the two adjacent teeth is located between one of the two windows and the recess.

2. The drill guide as recited in claim 1 wherein the recess is substantially v-shaped.

3. The drill guide as recited in claim 1 wherein the two windows each are defined by two parallel walls connected by a curved surface.

4. The drill guide as recited in claim 1 wherein a fastener is received in the window to secure an implant to bone.

5. A drill guide comprising:
    a handle; and
    at least one alignment tube including a body, a longitudinal axis, a bottom surface, a drill passage that aligns with a portion of the handle, a window that allows access to the drill passage, two adjacent teeth on the bottom surface that can contact bone, wherein a recess is located between the two adjacent teeth, and at least one of the two adjacent teeth is located between the window and the recess, wherein a fastener is received in the window to secure an implant to bone.

6. The drill guide as recited in claim 5 wherein the handle includes at least one opening that aligns with the drill passage of the at least one alignment tube.

7. The drill guide as recited in claim 5 wherein the at least one opening of the handle comprises two openings and the at least one alignment tube comprises two alignment tubes.

8. The drill guide as recited in claim 5 wherein the at least one alignment tube is substantially cylindrical.

9. The drill guide as recited in claim 5 wherein the at least one alignment tube includes a first end region attached to the handle and a second end region having the bottom surface that can contact bone.

10. The drill guide as recited in claim 9 wherein the recess is substantially v-shaped.

11. The drill guide as recited in claim 9 wherein the window has a length that extends substantially parallel to the longitudinal axis of the at least one alignment tube.

12. The drill guide as recited in claim 9 wherein the at least one alignment tube has a first length along the longitudinal axis, the window has a second length along the longitudinal axis, and the second length is less than half the first length.

13. The drill guide as recited in claim 5 wherein the window comprises two windows aligned with each other on opposing sides of the at least one alignment tube.

14. The drill guide as recited in claim 13 wherein a portion of the body is located between the two windows.

15. The drill guide as recited in claim 5 wherein the window is defined by two parallel walls connected by a curved surface.

* * * * *